(12) United States Patent
Dorn et al.

(10) Patent No.: US 8,819,583 B2
(45) Date of Patent: Aug. 26, 2014

(54) METHOD AND PROGRAM PRODUCT FOR PRODUCING MEDICAL FINDINGS ON THE BASIS OF MEDICAL IMAGE DATA

(75) Inventors: Karlheinz Dorn, Kalchreuth (DE); Subrata Sinha, Erlangen (DE); Vladyslav Ukis, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 444 days.

(21) Appl. No.: 12/715,721

(22) Filed: Mar. 2, 2010

(65) Prior Publication Data

US 2010/0229118 A1  Sep. 9, 2010

(30) Foreign Application Priority Data

Mar. 4, 2009  (DE) .......................... 10 2009 011 643

(51) Int. Cl.
*G06F 3/048* (2013.01)
(52) U.S. Cl.
USPC ........... 715/792; 715/764; 715/810; 715/781; 715/804
(58) Field of Classification Search
USPC .............................................. 715/810; 705/2
See application file for complete search history.

(56) References Cited

U.S. PATENT DOCUMENTS

| 2004/0003370 A1* | 1/2004 | Schenk et al. ................ 717/100 |
| 2006/0058624 A1* | 3/2006 | Kimura ......................... 600/407 |
| 2006/0177114 A1* | 8/2006 | Tongdee et al. ............... 382/128 |
| 2007/0238963 A1* | 10/2007 | Kaminaga et al. ........... 600/407 |
| 2008/0082966 A1 | 4/2008 | Dorn et al. |
| 2009/0279764 A1* | 11/2009 | Kaji et al. .................... 382/132 |

OTHER PUBLICATIONS

German Office Action dated Nov. 13, 2013 for corresponding German Application No. 10 2009 011 643.5.

* cited by examiner

*Primary Examiner* — Omar Abdul-Ali
*Assistant Examiner* — Sherrod Keaton
(74) *Attorney, Agent, or Firm* — Harness, Dickey & Pierce, P.L.C.

(57) ABSTRACT

In order to produce a set of medical findings based on image data which has been obtained by way of different imaging methods, a plurality of image viewer programs has hitherto been required. In at least one embodiment, a viewer device is to be provided, with which different image data can be viewed and with which it is simultaneously possible to produce a set of medical findings. According to at least one embodiment of the invention, a method is provided wherein a base page and at least one content page with display elements are selected and are loaded and activated by a program.

14 Claims, 2 Drawing Sheets

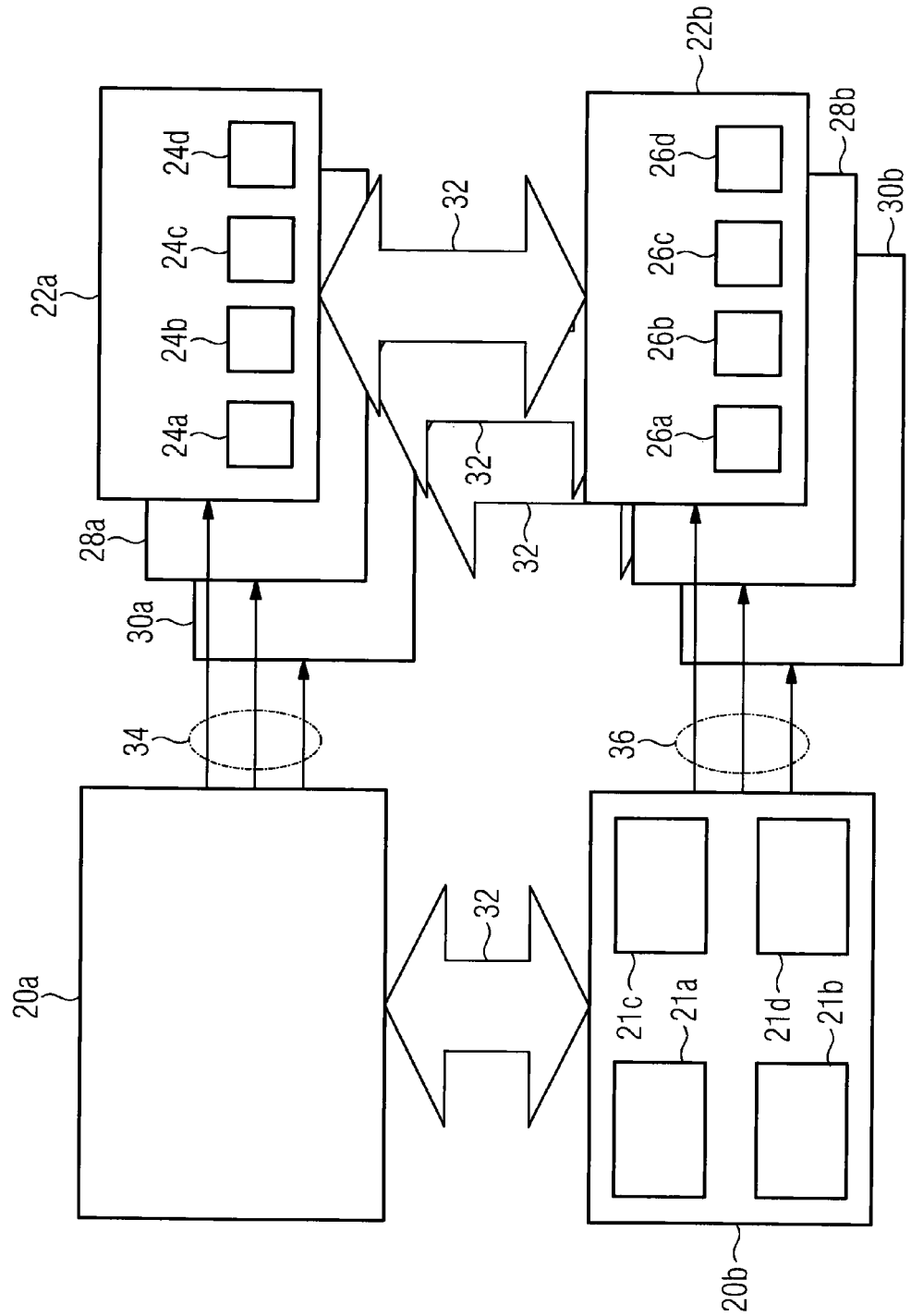

METHOD AND PROGRAM PRODUCT FOR PRODUCING MEDICAL FINDINGS ON THE BASIS OF MEDICAL IMAGE DATA

PRIORITY STATEMENT

The present application hereby claims priority under 35 U.S.C. §119 on German patent application number DE 10 2009 011 643.5 filed Mar. 4, 2009, the entire contents of which are hereby incorporated herein by reference.

FIELD

At least one embodiment of the invention generally relates to a method for generating a program, which enables the production of medical findings. At least one embodiment of the invention also generally relates to a method for enabling the production of medical findings on the basis of medical image data. Finally, at least one embodiment of the invention generally relates to a corresponding computer program product.

BACKGROUND

In order to produce a set of medical findings, doctors frequently utilize image data which has been obtained by means of different imaging methods. In this situation, this image data is often already present in a standardized data format. However, a wide variety of different image viewer programs are nevertheless needed in order to display and evaluate the data. That is to say, different graphical tools need to be made available in order to enable a doctor to evaluate the image data obtained in different ways so as to produce a set of findings.

It is thus desirable with regard to displaying digital x-ray images to have the ability to change the contrast of an image. On the other hand, three-dimensional models of organs, such as can be calculated for example from data from tomography images, should be capable of being rotated by an observer on a screen display. To this end, suitable control elements must be present.

In the majority of cases, software tools for evaluating the data must also be tailored to the type of image data. For example, a tool for determining lengths in the case of x-ray images must take into consideration a perspective distortion caused by the radiographic technique.

A doctor must therefore nowadays also use an image viewer program specially developed for the purpose for viewing image data which has been obtained by using a quite specific method.

If a doctor therefore now utilizes a plurality of imaging methods in order to be able to produce an improved set of findings, then he is forced to start and to use a corresponding number of image viewer programs. A set of findings produced whilst viewing the different image data are in turn prepared by the doctor using a separate program, a word processing program for example.

A quite similar problem results for developers of a medical recording device. For each new recording device which uses a new imaging method, it is also namely always necessary to develop a new image viewer program. Each time one of the new recording devices is sold, it is then also necessary for doctors to be instructed in how to operate the associated new image viewer program.

Such an additional development effort for a new image viewer program may actually also arise in the situation when an imaging method which has been implemented in an already developed recording device is improved. The associated image viewer program must then often also be adapted. In a hospital in which the corresponding recording device is already in use, there are in this situation possibly a great many computer workstations at which the image viewer program is already being used. The replacement of an image viewer program can then represent a very considerable outlay.

A method is known when using the computer program product PowerPoint® from the Microsoft® company in conjunction with the preparation of presentation slides, for a majority of presentation slides which are intended to exhibit a standardized division and a common slide frame, for forming each presentation slide by means of at least two subslides in each case. In this situation, the frame is determined by means of a subslide referred to as the master page. In addition, free fields are present on a master page. These fields are then filled with content by way of at least one further subslide, a so-called presentation page. By always using the same master page and different presentation pages it is then possible to produce presentation slides having a standardized organization.

SUMMARY

In at least one embodiment of the invention, a capability is provided when using an image viewer device to view and evaluate medical image data originating from different imaging methods in a standardized user environment and thereby to simultaneously produce a set of medical findings. With regard to the image viewer device, it should be possible with a minimum resource requirement to amend graphical tools for viewing image data which has been obtained using new imaging methods.

A method is disclosed in at least one embodiment for enabling the production of medical findings on the basis of medical image data. A method is disclosed in at least one embodiment for generating a program and a computer program product is disclosed in at least one embodiment. Advantageous developments of embodiments of the invention are also set down.

The method according to at least one embodiment of the invention for enabling the production of medical findings on the basis of medical image data comprises:

loading a base page and at least one content page, whereby display elements can be activated with the base page for generating an image display on the basis of image data and whereby at least one display element can be provided for a base page with the at least one content page, and activating the base page.

In this method, program code packages of a viewer program for an image viewer unit which are required in order to view and evaluate image data are therefore present separately from one another. They are then combined with one another in order to enable the production of medical findings. To this end, the program code packages are first loaded into the main memory (RAM—random access memory) of a computer. One of the program code packages, which is referred to here as the base page, is subsequently activated. When a base page is activated, this means that associated program code is executed by the computer, the program code therefore runs.

Different display elements are activated on a screen display by the base page. Such a display element may for example be a display for digital x-ray images or a display for those images which have been produced from data obtained by means of a computer tomography scanner. In addition, a display element can also comprise software tools with which, for example, the brightness of the display can be altered. In this situation, the base page only controls whether and where a display element appears on the screen display, but not the content of the display element. By replacing the display elements which are activated by a base page, displays for different image data can always be generated at the same location on the screen display. By this means, a standardized user environment is advantageously created.

A base page can additionally contain lists, menus and similar control elements. These remain available even if the display elements are replaced. In this situation, it is possible to provide a plurality of different base pages, from which a doctor can then select a favorite.

The display elements themselves are provided by other program code packages, the content pages. In this situation, a particular content page preferably makes available all those display elements belonging to a particular type of image data. There is therefore, for example, a content page which provides the display elements for displaying x-ray images, and a content page which provides the display elements for displaying tomography data. In this situation, a content page is not formed for image data relating to a particular patient. Rather, it includes program code which causes data from, for example, digital x-ray images of a patient to be accepted by the content page and an image display to be generated on a screen on the basis of the data.

Like the base page, the content pages are loaded into the main memory of the computer. By loading particular content pages, it is possible to define which image data can be viewed.

The base page has the ability to activate individual display elements of the content pages. Similar to what happens in a situation of the base page being activated, this activation causes corresponding program code of the content page to run. The display elements then appear on a screen in an area which the base page has assigned to the display elements. By this means it is therefore possible to control through the base page when and where a content page appears on a screen display.

Base pages and content pages are preferably provided as self-contained files in which the corresponding program code is stored. If for example a new recording device is then put into operation, only one corresponding new content page therefore needs to be provided in order to view the image data obtained therewith. In particular, no complete new viewer program needs to be developed because an already existing base page can be used in order to activate the display elements of the new content page.

A base page already known to a user of the program, with the operation of which said user is familiar, is therefore always displayed to said user. The new content page then provides the suitable display elements for viewing image data which has been generated using the new recording device. By means of the method, a standardized user environment is thus advantageously always made available to a user by the base page, into which can be integrated display elements for different image data.

The method of at least one embodiment is advantageously developed by the following:
receiving an input for the purpose of selection by a user on the basis of the base page, and
activating at least one display element of a content page depending on the selection.

Should a doctor wish to view other image data whilst producing a set of findings, he therefore only needs to select a different content page. The selection preferably takes place by means of a menu, which a user uses to select from image data which is available from a patient. Provision can however also be made to enable the selection by means of a different program and to convey only the result of the selection to the base page. Which display elements of which content page are then to be activated can be determined by the base page independently on the basis of the selected image data.

A display element of a content page, which may be currently visible on the screen at the time of the selection, is naturally deactivated as necessary by the base page in this situation. The display element then disappears from the screen. As a result of the deactivation, the space required for the display elements to be activated is thus generated on the screen.

Consequently, different images can therefore be displayed in succession in a standardized user environment for the base page. However, by activating a plurality of display elements of different content pages, image data having different origins can also be displayed at the same time.

As a result of displaying different image data in a standardized user environment (successively or simultaneously), this yields the advantage that an easily used system with which medical findings can be produced on the basis of the different image data is available to a user, in other words to a doctor for example.

The method of at least one embodiment is furthermore advantageously developed by the following:
receiving at least one input for the purpose of definition of a text by a user on the basis of the base page,
storing the defined text.

In this context, a definition of texts can reside in a user entering texts using a keyboard, dictating them or simply marking ready prepared text passages. As texts can be defined and stored by way of the base page, this yields the advantage that a user can produce one set of findings whilst evaluating different image data. For example, a doctor can first view images of captured x-ray images by means of the display elements of a content page for x-ray data. On the basis of these images he produces a first partial set of findings which he records for example by entering a text in an input field of the base page. He can then switch the display elements and for example have tomography data or magnetic resonance imaging data displayed. The text for the partial set of findings produced on the basis of the x-ray images is not lost in this situation because this text is part of the base page. On the basis of the further images displayed, the doctor can then supplement the text and thus expand the set of findings.

The method according to at least one embodiment of the invention for generating a program, which enables the production of medical findings, comprises:
providing at least one program code package for a base page, by which display elements can be activated,
providing at least one program code package for a content page, by which display elements can be provided for a base page,
providing a program code package for a program for loading and activating a program code package for a base page and for loading at least one program code package for a content page,
combining all the program code packages in a computer readable form on at least one data medium of a data processing installation,
selecting a base page and at least one content page.

A program code package can comprise one or more files, which can contain source code or actual computer readable binary code. Combination is preferably understood as storage, linking and storage, or where applicable also compilation, linking and storage.

The method yields the advantage that in order to tailor the program to a new imaging method only a small part of the entire program actually needs to be reprogrammed. That is to say, only one further program code package needs to be developed for a content page having display elements for displaying data for the new method. Subsequently, these new content pages can be selected and activated like already existing content pages. A set of medical findings can then thus be produced by the new imaging method on the basis of the image data.

A further advantage resides in the fact that a program code package for a content page can also be integrated particularly easily into the program in the situation when the program is for example already being used in a hospital. The program code package for the new content page must then simply be added to the program code packages already present. If the new content page is then selected, the corresponding display elements are available.

In an advantageous manner, the selection is passed by way of a file in an XML format (XML—Extensible Markup Language) to the program for loading and activation. Such a file can also be easily read by an operator and can be adapted by said operator without a special programming environment. In other words, an operator can generate a new image viewer program quite simply by changing the file. So long as all selected program code packages for the base page and the content pages are already present in computer readable form, no further procedural step is required.

By this, it is possible in a particularly simple manner to develop a new version of a program which enables the production of medical findings. All the program code packages can be prepared and from these can be generated an image viewer program, which is individually tailored for a customer, by providing a file having a selection of particular program code packages.

Instead of a file being used, it is however also possible to integrate a content page into the program while the program is already running. This can come about in such a way that a program code package for the content page is loaded by the program into the memory as a module.

The method is developed in an advantageous manner if for the at least one program code package for a content page, in addition, separate program code for processing data for an image display is provided, depending on a user input.

In other words, in a program code package for a content page the program parts for generating the display elements on a screen and the program parts for processing the data are strictly separated. Processing the data here resides in changing the data depending on a user input, such as is required for example when altering the contrast of an x-ray image or when rotating a three-dimensional model of an organ. The separation of the two program parts offers the advantage that the two program parts can be developed and improved independently of one another.

A further advantageous development of at least one embodiment of the method results if for the at least one program code package for a base page, in addition, separate program code for loading data to be used for an image display is provided.

With regard to this development, the data which is displayed by the content pages, and where applicable processed for that purpose, is loaded into a main memory of a computer by the base page and not by the content page itself. Any development of new content pages is greatly simplified as a result. The loading of the data into the memory does not need to be programmed separately for each content page. The data in question is preferably medical image data.

In a comparable manner, an advantage results if it should be made possible to load stored data into the main memory in a new format. That is to say, only the base page then needs to be adapted. All the content pages which then access the data in the main memory can be supplied automatically with data which is stored in the new format.

Finally, an advantageous development of at least one embodiment of the method results if for the at least one program code package for a base page, in addition, program code is provided, through which a position of activated display elements on at least one screen is defined depending on a user selection. This means that a user is able to adapt the position of the display elements on a screen to suit his requirements when producing a set of findings.

At least one embodiment of the invention also comprises a computer program product having at least one computer readable data medium, whereby the following are stored on the at least one computer readable data medium:

a program code unit which is designed to load and to activate program code for a base page and also to load program code for at least one content page, a program code unit which is designed to provide at least one base page, a program code unit which is designed to provide at least one content page.

This computer program product offers a generic program for viewing image data and for producing a set of findings. Through selection of a base page and at least one content page it is namely possible in a simple manner to generate a program tailored to the requirements of a user.

BRIEF DESCRIPTION OF THE DRAWINGS

The invention will be described in detail in the following with reference to example embodiments, in which;

FIG. 2 shows a schematic illustration of program code packages, which have been loaded into a main memory of a computer by a loader program, whereby the program code packages and the loader program form an embodiment of a computer program product according to the invention.

DETAILED DESCRIPTION OF THE EXAMPLE EMBODIMENTS

Figure 1:
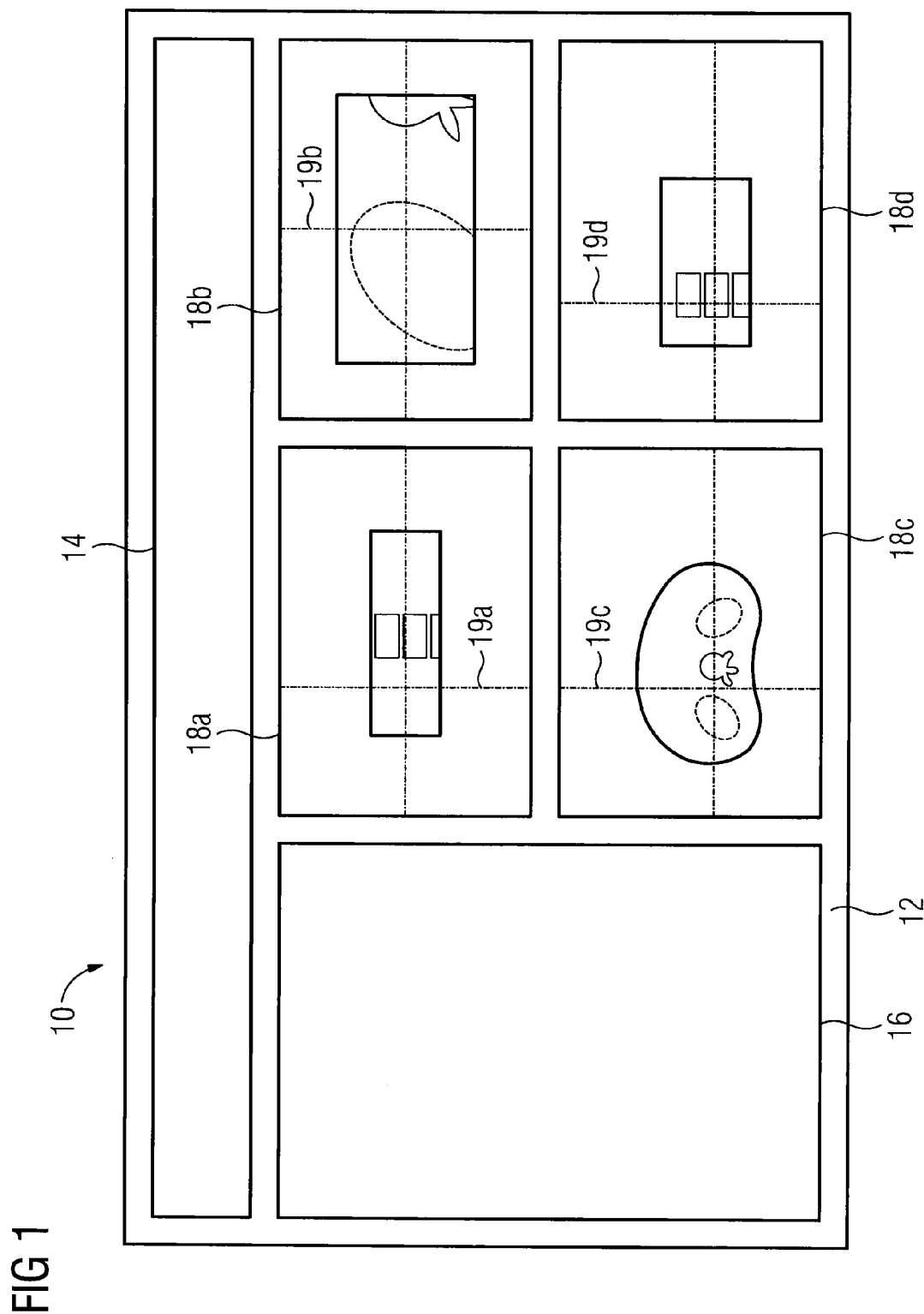
FIG. 1 shows a schematically represented user interface on a screen, as has been generated by an embodiment of the method according to the invention in order to enable the production of medical findings.

Various example embodiments will now be described more fully with reference to the accompanying drawings in which only some example embodiments are shown. Specific structural and functional-details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The user interface 10 shown in FIG. 1 is displayed on a screen of a computer (not shown in detail in FIG. 1) in a hospital. The user interface 10 belongs to an image viewer program which enables a doctor to view different medical images of a patient and at the same time to produce a set of medical findings.

On starting, the image viewer program is formed by a loader program from a plurality of separate program code packages. To this end the loader program loads the program code packages into a main memory of the computer.

A first program code package is a program code package for a base page, by which a graphical background 12, a selection bar 14 and a findings field 16 are generated on the user interface 10 on the screen. As a result of program code for the base page, in a graphics memory of the computer, by way of which the colors of pixels of the screen are controlled depending on the contents of corresponding memory cells of the graphics memory, such memory contents are correspondingly defined. In this situation, the memory contents are chosen such that the background 12, the selection bar 14 and the findings field 16 of the base page are displayed on the user interface 10. Only outlines of the selection bar 14 and the findings field 16 are shown in FIG. 1.

Further program code, through which functionalities described further below are enabled, is associated with the base page.

Four further display fields 18a to 18d are displayed on the user interface 10. The display fields 18a to 18d are not generated by program code for the base page. Rather, they belong to a second program code package, from which the image viewer program has been formed. This second program code package forms a content page which provides the display fields 18a to 18d for displaying tomography data. In order for the display fields 18a to 18d to appear on the user interface 10 they must be activated by the base page. To this end, firstly a position and a size are assigned to each of the display fields 18a to 18d by the base page. This assignment is made by storing the position and the size in an area of the main memory. The base page subsequently calls up an activation function for the content page.

As a result of calling the activation function, program code from the program code package for the content page is executed, which first causes the position and the size to be read from the area of the main memory and subsequently causes graphical representations of tomography data to be displayed on the user interface 10 in accordance with the assigned positions and sizes. For the display process, corresponding memory contents are defined in the graphics memory by the program code for the content page. The graphical representations form the visible display fields 18a to 18d.

By way of the selection bar 14, a user of the image viewer program can select for which patient he would like to produce a set of findings and which images of the patient he would like to view for this purpose. This selection can also take place indirectly by way of a different program, as described further below.

When a user of the image viewer program selects a patient by way of the selection bar 14, corresponding patient data is loaded into the main memory of the computer from a database server by the base page by way of a data network to which the computer is connected. A list containing the available types of images, in other words x-ray images or magnetic resonance images for example, is then displayed to the user through the selection bar 14. By using a computer mouse or a comparable input device the user can select a list entry. Depending on the list entry selected, associated program code for the base page is allowed to run, which causes the image data of the selected type to be loaded into the main memory from another storage medium. Such a storage medium can be a hard disk of the computer, or an NAS (network attached storage) from which data can be received over the data network.

If the selection is made indirectly by way of a different program, such as by way of a database for patient data for example, then data concerning the selection of image data is conveyed by this program to the image viewer program. Within the viewer this data is evaluated by program code for the base page, similar to what happens when a selection is made by way of the selection bar 14.

The user can record in written form in the findings field 16 a set of findings prepared on the basis of images displayed. To this end, in the example illustrated the user enters a text, by using a keyboard (not shown in FIG. 1) of the computer, which initially is stored by the program code for the base page in an area provided for the purpose, managed by the base page, of the main memory of the computer. In addition, the entered text is displayed in the findings field 16 by way of suitable control commands by altering the memory contents in the graphics memory of the computer.

In the example shown in FIG. 1, the user has selected tomography data for the patient. In order to display images corresponding to the tomography data, the base page has activated four display fields 18a, 18b, 18c, 18d. Images captured from different perspectives which have been calculated from the tomography data are displayed in the display fields 18a, 18c and 18d. A detail enlargement from the display field 18c is also shown in the display field 18b.

Because the tomography data has already been loaded into the main memory by the base page, the content page then only needs to contain program code for displaying the tomography data. To this end, color values of pixels of an image, which the tomography data or parts thereof represents graphically are calculated through the program code. In accordance with the calculated color values, contents of individual memory cells are defined in the graphics memory of the computer memory. Which memory cells in the graphics memory may be used by the program code for the content page in order to display the image is defined by the base page. To this end, an area on the screen in which the calculated image is to appear is determined by the base page. By means of a content page it is also possible to calculate and display a plurality of images. In this situation, each image displayed forms one display field.

The content page also makes available measuring tools 19a to 19d for measuring lengths of organs of the patient which can recognized in the corresponding display fields 18a to 18d. The measuring tools 19a to 19d are operated by a user by using the computer mouse to mark positions in the display fields 18a to 18d on the screen whose separation distance is to be calculated. The signals which are generated by pressing buttons on the computer mouse to mark the positions are evaluated by program code for the content page.

The distances measured are conveyed to the base page, stored in an area managed by the base page of the main memory and additionally displayed in the findings field 16 in the manner described in connection with the input of a text for a set of findings.

The user can subsequently select other images from the patient, x-ray images for example, by way of a corresponding list in the selection bar 14. This causes a program code unit for the base page associated with the list entry to be executed, through which firstly a deactivation function of the content page is called up for tomography data. This call causes the program code for the content page for tomography data to run, which clears the display fields 18a to 18d of the user interface 10. To this end, corresponding memory contents of the graphics memory are altered by the program code.

The program code for the base page subsequently continues running, through which an activation function of a content page is then called up for x-ray data. This allows program code for the content page for x-ray data to run, as a result of which a display of display fields of the content page for x-ray images is effected. This happens in comparable fashion to that already described in connection with the activation function of the content page for tomography data. The content page for x-ray images is a self-contained, third program code package which forms one of the components of the viewer program.

The dimensions of organs read off from the tomography data by way of the measuring tools 19a to 19d are not lost in the case of a switch of the display fields on the user interface 10 because they are stored in the area of the main memory managed by the base page.

After the user has completed the set of findings, he can have it stored on a storage medium not shown in FIG. 1 by operating a control element (not shown further in FIG. 1) of the findings field 16 from the base page. To this end, by using the computer mouse the user generates a control signal for the control element, whereupon program code for the base page runs, which brings about a transfer of the data stored in connection with the set of findings from the corresponding areas in the main memory to another storage medium or to a patient database.

In FIG. 2, in relation to the image viewer program which is described in connection with FIG. 1, those program code packages are shown which have been loaded into the main memory of the computer by the loader program.

FIG. 2 illustrates symbolically that each of the program code packages which constitute the components of the image viewer program is composed of two program parts in each case. They will be described in detail in the following. The program parts can be developed separately in each case by developers of the computer program product.

The background 12, the selection bar 14 and the findings field 16 shown in FIG. 1 are part of a program code unit which in FIG. 2 forms a first program part of the base page, namely a so-called frontend 20a of the base page. The frontend 20a includes in total that program code through which graphical elements of the base page are displayed on the user interface 10 shown in FIG. 1. In other words, it includes that program code which alters memory contents of the graphics memory of the computer. The program code for the frontend 20a also accepts signals from the computer mouse, when for example a user uses it to make a selection from a list in the selection bar 14. In the same way, signals from the keyboard are accepted when a text is entered in the findings field 16.

The actual management and processing of data within the base page on the other hand are effected by a different program part. This part of the program code package for the base page forms a so-called backend 20b for the base page. The backend 20b is formed from separate software modules. In particular, the backend 20b comprises a software module 21a which effects the loading of data, a software module 21b which makes the loaded data available simultaneously for a plurality of display elements, a software module 21c which prepares the data for display using different display elements, and finally a software module 21d with which texts relating to a set of findings can be managed and stored.

The program code for the backend 20b also evaluates the signals from the keyboard and the computer mouse accepted by the frontend 20a.

The graphical elements of the display fields 18a to 18d with the graphical elements of the measuring tools 19a to 19d shown in FIG. 1 are likewise generated by separately developed program code, namely the program code package for the content page for the tomography data. This is also divided into a frontend 22a and a backend 22b. The program code for generating graphical elements on the screen is contained in the frontend 22a as in the case of the base page. The frontend 22a also accepts signals from the computer mouse and the keyboard if these signals have been generated in connection with a graphical element of the content page. In this situation, the connection can be established by means of a cursor which is moved on the screen by the computer mouse to a position of a graphical element of the content page.

Within the frontend 22a of the content page the graphical elements of each display fields are generated by program code, which is in each case a separate software module 24a, 24b, 24c, 24d.

In addition to the actual display of the tomography data in the display fields on the screen, calculations are however also to be carried out. For example, in order to form the pixels for the enlarged display of a tomography image in the display field 18b shown in FIG. 1 corresponding data needs to be extracted from the totality of the tomography data. This is not performed by the associated software module 24b.

Instead, a software module 26b of the backend 22b is assigned to the software module 24b. Through this software module 26b of the backend 22b are performed the calculations which are necessary for a desired type of display of the data. Corresponding software modules 26a, 26c, 26d of the backend 22b for processing image data are also assigned to the other software modules 24a, 24c, 24d of the frontend 22a. In each case, one of the software modules 24a to 24d of the frontend 22a together with the software module 26a to 26d of the backend 22b assigned to it generates a display element including the functionalities associated therewith, such as for example a capability to alter the contrast of an image.

FIG. 2 also shows that in addition to the frontend 22a and the backend 22b of the content page for tomography data a further two-part program code package having a frontend 28a and a backend 28b of the content page described in connection with FIG. 1 for x-ray data also belongs to the computer program product. Finally, the computer program product also contains a further program code package for a content page for magnetic resonance images. This program code package is also divided into a frontend 30a and a backend 30b.

Not illustrated in FIG. 2 are individual software modules of the frontend 28a and 30a and corresponding software modules of the backend 28b and 30b.

The software modules of the frontend 20a, 22a, 28a, 30a exchange data with the assigned software modules of the backend 20b, 22b, 28b, 30b by way of communication channels 32. A communication channel 32 is a logical structure which is provided in the program code packages through functions. Therefore, for example, in order to initiate a processing of data in the main memory by an assigned software module of the backend from a software module of a frontend, which has accepted a signal from a computer mouse, a suitable function of the software module of the backend is called up from the software module of the frontend. When the function is called, this causes program code, forming the function, in the software module of the backend to run, by which the data is processed in the desired manner.

From the frontend 20a of the base page, display fields of a frontend 22a, 28a, 30a are activated by virtue of the fact that an activation function for the corresponding frontend 22a, 28a, 30a is called up. This form of influence of the frontend 20a on the frontend 22a, 28a, 30a is symbolized in FIG. 2 by arrows 34. The mode of action of calling up an activation function has already been described in connection with FIG. 1.

Correspondingly, the backend 20b of the base page can also convey the position of loaded data in the main memory of the computer to the backends 22b, 28b, 30b of the content pages, by way of calling up a function, similar to the case of the activation functions. This is also symbolized in FIG. 2 by way of arrows 36.

The examples in FIG. 1 and FIG. 2 show how at least one embodiment of the invention makes it possible to provide a standardized user environment for viewing and evaluating medical image data, with which a set of medical findings can be produced at the same time. The user environment is also simple to extend.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

| List of reference characters | |
|---|---|
| 10 | User interface |
| 12 | Graphical background |
| 14 | Selection bar |
| 16 | Findings field |
| 18a to 18d | Display field |
| 19a to 19d | Measuring tool |
| 20a, 22a, 28a, 30a | Frontend |
| 20b, 22b, 28b, 30b | Backend |
| 21a, 21b, 21c, 21d | Software module |
| 24a to 24d | Software module |
| 26a to 26d | Software module |
| 32 | Communication channel |

What is claimed is:

1. A method for enabling the production of medical findings on the basis of medical image data, comprising:
providing separate self-contained program code package files for a base page and at least one content page, the program code package for the base page configured to activate display elements, the at least one program code package for the content page configured to provide the display elements for the base page, such that
the display elements are activateable with the base page for generating an image display on the basis of the medical image data, and
at least one display element is provideable for the base page with the at least one content page;
providing a loader program for forming an image viewer program from the plurality of separate program code packages, the loader program for loading and activating the program code package for the base page and for loading the at least one program code package for the content page;
loading the base page and the at least one content page using the loader program; and
activating the base page.

2. The method as claimed in claim 1, further comprising:
receiving an input for selection by a user on the basis of the base page, and
activating at least one display element of the at least one content page depending on the selection.

3. The method as claimed in claim 1, further comprising:
receiving at least one input for definition of a text by a user on the basis of the base page, and
storing the defined text.

4. A method for generating a program, which enables the production of medical findings, comprising:
providing at least one program code package for a base page, the at least one program code package for the base page configured to activate display elements;
providing at least one program code package for a content page, the at least one program code package for the content page configured to provide the display elements for the base page, the at least one program code package for the base page and the at least one program code package for the content page are separate, self-contained files;
providing a program code package for a loader program for loading and activating the at least one program code package for the base page and for loading the at least one program code package for the content page, the loader program being configured to form an image viewer program from the at least one program code package for the base page and the at least one program code package for the content page;
combining the at least one program code package for the base page, the at least one program code package for the content page and the program code package for the loader program in a computer readable form on at least one data medium of a data processing installation; and
selecting the base page and the at least one content page.

5. The method as claimed in claim 4, wherein the selection is passed by way of a file in an XML format to the loader program for loading and activation.

6. The method as claimed in claim 4, wherein for the at least one program code package for the content page, in addition, separate program code for processing data for an image display is provided, depending on a user input.

7. The method as claimed in claim 4, wherein for the at least one program code package for the base page, in addition, separate program code for loading data to be used for an image display is provided.

8. The method as claimed in claim 4, wherein for the at least one program code package for the base page, in addition, program code is provided, through which a position of activated display elements on at least one screen is defined depending on a user selection.

9. A computer program product having at least one non-transitory computer readable data medium, whereby at least the following are stored on the at least one non-transitory computer readable data medium:
a program code unit configured to load and to activate program code for at least one base page and also to load program code for at least one content page;
a program code unit configured to provide the at least one base page; and
a program code unit configured to provide the at least one content page, the program code unit for the base page configured to activate display elements, the at least one program code unit for the content page configured to provide the display elements for the base page, wherein the program code unit of the at least one base page and the program code unit of the at least one content page are each provided as a separate self-contained file and wherein the program code unit configured to load and activate the base page is configured to form an image viewer program from the separate program code units of one of said the at least one base page and from the at least one content page.

10. The method as claimed in claim 2, further comprising: receiving at least one input for definition of a text by a user on the basis of the base page, and storing the defined text.

11. The method as claimed in claim 5, wherein for the at least one program code package for the content page, in addition, separate program code for processing data for an image display is provided, depending on a user input.

12. A non-transitory computer readable medium including program segments for, when executed on a computer device, causing the computer device to implement the method of claim 1.

13. The method of claim 1, wherein each of the program code package file for the base page and the program code package file for the content page include a front end and a back end, the front end of the program code package file for the base page being linked to the front end of the program code package file for the content page and the back end of the program code package file for the base page being linked to the back end of the program code package file for the content page.

14. The method of claim 4, wherein each of the at least one program code package for the base page and the at least one program code package for the content page include a front end and a back end, the front end of the at least one program code package for the base page being linked to the front end of the at least one program code package for the content page and the back end of the at least one program code package for the base page being linked to the back end of the at least one program code package for the content page.

* * * * *